(12) United States Patent
Keene

(10) Patent No.: US 8,196,896 B2
(45) Date of Patent: Jun. 12, 2012

(54) COMBINATION FLOW THROUGH INJECTION AND ISOLATION VALVE FOR HIGH PRESSURE FLUIDS

(75) Inventor: Russell Keene, Sudbury, MA (US)

(73) Assignee: Waters Technologies Corporation, Milford, MA (US)

( * ) Notice: Subject to any disclaimer, the term of this patent is extended or adjusted under 35 U.S.C. 154(b) by 720 days.

(21) Appl. No.: 10/597,990

(22) PCT Filed: Mar. 4, 2005

(86) PCT No.: PCT/US2005/007005
§ 371 (c)(1), (2), (4) Date: Aug. 15, 2006

(87) PCT Pub. No.: WO2005/089124
PCT Pub. Date: Sep. 29, 2005

(65) Prior Publication Data
US 2007/0137713 A1    Jun. 21, 2007

Related U.S. Application Data

(60) Provisional application No. 60/550,930, filed on Mar. 5, 2004.

(51) Int. Cl.
 *F16K 1/44* (2006.01)
(52) U.S. Cl. ............................. 251/174; 73/61.55
(58) Field of Classification Search ............... 251/149.9, 251/157, 159, 161, 170, 171, 188, 190, 310, 251/317.01; 73/61.55, 61.56, 863.82; 137/625.43
See application file for complete search history.

(56) References Cited

U.S. PATENT DOCUMENTS

| 2,436,680 A | 2/1948 | Straussler |
| 2,972,888 A | 2/1961 | Lamkin |
| 3,116,642 A | 1/1964 | Weir |

(Continued)

FOREIGN PATENT DOCUMENTS

JP    45-7018 B    4/1970

(Continued)

OTHER PUBLICATIONS

Interrogation (Japanese and English translation) mailed Jan. 17, 2012 issued by Japan Patent Office in related Japanese application No. 2007-501998 (13 pages).

*Primary Examiner* — John Fox
(74) *Attorney, Agent, or Firm* — Waters Technologies Corporation

(57) ABSTRACT

A flow through injection valve having a stationary member, a movable member, a surface of the stationary member interfacing with a surface of the movable member; and at least one pin isolation valve having a flow through internal conduit and movably positioned so that the internal conduit can interface with at least one flow through conduit in the movable member. The pin isolation valves are movably positioned so that the internal conduit is also capable of fluidically communicating with another flow through internal conduit in the movable member. The flow through injection valve can be combined with a similar flow through isolation valve to serve as a multiple valve and typically for replacing a conventional face seal valve of a high pressure liquid chromatography (HPLC) system. The multiple valve allows flow to be transferred through without need for switching or rotating under high pressure. Movement is by rotation or translation.

4 Claims, 9 Drawing Sheets

U.S. PATENT DOCUMENTS

| | | | |
|---|---|---|---|
| 3,119,251 A | | 1/1964 | Bowers |
| 3,350,055 A | * | 10/1967 | Campbell et al. ............ 251/89.5 |
| 3,370,612 A | * | 2/1968 | Holl ......................... 137/625.47 |
| 3,580,540 A | * | 5/1971 | Heinen ........................ 251/159 |
| 3,630,371 A | | 12/1971 | Hrdina |
| 3,961,534 A | | 6/1976 | Gundelfinger |
| 4,298,026 A | | 11/1981 | Ambers |
| 4,476,731 A | | 10/1984 | Charney |
| 4,793,591 A | * | 12/1988 | Decker et al. ................ 251/172 |
| 5,105,851 A | * | 4/1992 | Fogelman ................ 137/625.11 |
| 5,265,483 A | | 11/1993 | Farrell et al. |
| 5,616,300 A | | 4/1997 | Ford et al. |
| 6,112,767 A | | 9/2000 | Pinkham et al. |
| 6,155,123 A | | 12/2000 | Bakalyar |
| 6,318,157 B1 | | 11/2001 | Corso |
| 6,365,105 B1 | | 4/2002 | Waters et al. |

FOREIGN PATENT DOCUMENTS

| | | |
|---|---|---|
| JP | 59-195565 A | 12/1984 |
| JP | 63-160475 A | 10/1988 |
| JP | 06-185641 A | 7/1994 |
| JP | 07-071629 A | 3/1995 |
| JP | 2001-065714 A | 3/2001 |

* cited by examiner

COMBINATION FLOW THROUGH INJECTION AND ISOLATION VALVE FOR HIGH PRESSURE FLUIDS

CROSS REFERENCE RELATED APPLICATION INFORMATION

This application claims priority from U.S. Provisional Patent Application No. 60/550,930, filed Mar. 5, 2004. The contents of these applications are incorporated herein by reference.

BACKGROUND OF THE INVENTION

The invention relates generally to the field of high pressure fluids and, more specifically, to a combination of multiple isolation valves that permit introduction of flow path without interruption of flow from the fluid source.

DESCRIPTION OF RELATED ART

Conventional 6-port face shear valves, also referred to as face seal valves, used in high pressure liquid chromatography (HPLC) provide ports that interface with the sample, the syringe, the pump, the column and the two ends of the sample loop. Such face seal valves must be rotated to switch from one port to another. The rotation of the face seal under high pressure inherently causes damage to the plastic mating surfaces because the fluid port openings must slide against the rotor surface causing fatigue of the rotor material. This results in shortened face seal valve life. In addition, it is necessary to temporarily block flow during the sample injection process and sample dispersion occurs.

At higher chromatography pressures, e.g., greater than 15,000 psig or 100 MPa, what is needed is a flow-through isolation sample injection valve that can provide high sample injection life with minimal sample distortion and minimal pump pressure pulsing.

BRIEF SUMMARY OF THE INVENTION

To address the above and other issues, the present invention describes a combination of multiple flow-through high pressure isolation valves for high pressure fluids, and which is particularly suitable for use in HPLC applications as a substitute for the conventional face shear valve.

It is an object of this invention to provide a flow-through sample injection valve with fluid port openings that do not slide against a rotor surface causing fatigue of the rotor material.

It is another object of this invention to provide a flow-through sample injection valve which avoids flow of the sample through non-cylindrical passages so as to minimize sample dispersion.

In a particular aspect of the invention, the present invention is directed to a flow through injection valve, the flow through injection valve comprising:
a stationary member; a movable member, a surface of the stationary member interfacing with a surface of the movable member; and at least one pin isolation valve. The at least one pin isolation valve has a flow through internal conduit, and is movably disposed so that the internal conduit is capable of fluidically communicating with at least one flow through conduit in the movable member, and is movably disposed so that the internal conduit is capable of fluidically communicating with another flow through conduit in the movable member. The movable member of the flow through injection valve can further comprise first and second conduits for interfacing with internal conduits of first and second pin isolation valves, with the first and second conduits opening to a surface of the movable member; a third conduit enabling fluidic communication between the internal conduits of the first and second pin isolation valves; and a fourth conduit enabling fluidic communication between internal conduits of third and fourth pin isolation valves, the third pin isolation valve providing fluid flow, the fourth pin isolation valve exhausting the fluid flow. The movable member can move by rotation around an axis of rotation or by at least one of linear and curvilinear translation. One of the at least one pin isolation valves can be fluidically coupled to a sample loop of a high pressure liquid chromatography (HPLC) system. One of the at least one pin isolation valves can be in fluidic communication with a pump supplying high pressure liquid to a high pressure liquid chromatography (HPLC) system. One of the at least one pin isolation valves can be fluidically coupled to a column discharging high pressure liquid from a high pressure liquid chromatography (HPLC) system.

In a specific aspect of the invention, the present invention is directed to a flow through injection valve, the flow through injection valve disposed around an axis of rotation, the injection valve comprising: at least two opposing valve ends disposed around the axis of rotation; the movable member comprising a rotor disposed between said valve ends, an axis of rotation of the rotor being one of parallel and coincident with the axis of rotation of the injection valve, and the rotor is disposed such that orientation of the rotor can change by rotation around the axis of rotation of the rotor. The rotor has an outer surface; at least two opposing surfaces each intersecting the outer surface; a first flow-through conduit having an opening on a first of the at least two opposing surfaces and an opening on a second of the at least two opposing surfaces; a second flow-through conduit having an opening on a first of the at least two opposing surfaces and an opening on a second of the at least two opposing surfaces; a flow through conduit having an opening on the outer surface and an opening on the first of the at least two opposing surfaces; and a flow through conduit having an opening on the outer surface and an opening on the second of the at least two opposing surfaces. The rotor further comprises a first sealing annulus for sealing the openings on the first of the at least two opposing surfaces; and a second sealing annulus for sealing the openings on the second of the at least two opposing surfaces.

The rotor further comprises a first pin isolation valve having an internal conduit, the first pin isolation valve disposed to move parallel to the axis of rotation of the injection valve, with the first pin isolation valve movably disposed so as to be capable of fluidically communicating, through said internal conduit, with the opening on the first flow-through channel on the first of the at least two opposing surfaces, and movably disposed so as to be capable of fluidically communicating, through the internal conduit, with the flow through conduit having an opening on the outer surface and an opening on the second of the at least two opposing surfaces. The rotor further comprises a second pin isolation valve having an internal conduit, the second pin isolation valve disposed to move parallel to the axis of rotation of the injection valve, and movably disposed so as to be capable of fluidically communicating, through the internal conduit, with the opening on the first flow-through channel on the second of the at least two opposing surfaces, and movably disposed so as to be capable of fluidically communicating, through the internal conduit, with the flow through conduit having an opening on the outer surface and an opening on the second of the at least two opposing surfaces.

The rotor further comprises a third pin isolation valve having an internal conduit, the third pin isolation valve disposed to move parallel to the centerline of the injection valve, the third pin isolation valve movably disposed so as to be capable of fluidically communicating, through the internal conduit, with the opening on the second flow-through channel on the first of the at least two opposing surfaces, and movably disposed so as to be capable of fluidically communicating, through the internal conduit, with the flow through conduit having an opening on the outer surface and an opening on the second of the at least two opposing surfaces. The rotor further comprises a fourth pin isolation valve having an internal conduit, the fourth pin isolation valve disposed to move parallel to the centerline of the injection valve, the fourth pin isolation valve movably disposed so as to be capable of fluidically communicating, through the internal conduit, with the opening on the second flow-through channel on the second of the at least two opposing surfaces, and movably disposed so as to be capable of fluidically communicating, through the internal conduit, with the flow through conduit having an opening on the outer surface and an opening on the second of the at least two opposing surfaces.

The rotor can further comprise: a rotor clamp having an outer surface and an inner surface, the inner surface surrounding at least a portion of the outer surface of the rotor; a first opening on the outer surface of the rotor clamp penetrating the rotor clamp to coincide with the first opening on the outer surface of the rotor; and a second opening on the outer surface of the rotor clamp penetrating the rotor clamp to coincide with the second opening on the outer surface of the rotor. The rotor clamp can further comprise drive means for driving the rotor to rotate around the axis of rotation of the rotor. The rotor clamp drive means can comprise a gear drive operator or a handle operator.

At least one of the valve ends can comprise: a stator enclosing the at least one pin isolation valve, the stator adjacent to the rotor; a sealing layer enclosed within the stator and enclosing the at least one pin isolation valve for sealing the at least one pin isolation valve; a Belleville spring washer; a Belleville spring; a load washer; and a spherical nut, the Belleville spring washer, the Belleville spring, the load washer and the spherical nut axially arranged to impose an axial force for sealing the sealing layer enclosing the pin isolation valve. Either of the first and second pin isolation valves can be fluidically coupled to a sample loop of a high pressure liquid chromatography (HPLC) system. Either of the third and fourth pin isolation valves can be in fluidic communication with a pump supplying high pressure liquid to a high pressure liquid chromatography (HPLC) system or in fluidic communication with a column discharging high pressure liquid to a high pressure liquid chromatography (HPLC) system.

In another embodiment, the present invention is directed to a multiple valve comprised of: a housing; a rotary flow through isolation valve disposed within the housing, with the isolation valve oriented in an axial direction for isolation of fluid flow, the isolation valve disposed around an axis of rotation, the isolation valve comprising: at least two opposing valve ends disposed around the axis of rotation; a rotor disposed between the valve ends, an axis of rotation of the rotor being substantially parallel and coincident with the axis of rotation of the isolation valve, with the rotor disposed such that orientation of the rotor can change by rotation around the axis of rotation of the rotor. The rotor has: an outer surface, at least two opposing surfaces each intersecting the outer surface; a flow-through conduit having an opening on a first of the at least two opposing surfaces and an opening on a second of the at least two opposing surfaces; a flow through conduit having an opening on the outer surface and an opening on the first of the at least two opposing surfaces; a flow through conduit having an opening on the outer surface and an opening on the second of the at least two opposing surfaces; at least one blank opening on the first of the at least two opposing surfaces; and at least one blank opening on the second of the at least two opposing surfaces. The rotor further comprises: a first sealing annulus for sealing the openings on the first of the at least two opposing surfaces, and a second sealing annulus for sealing the openings on the second of the at least two opposing surfaces. The rotor further comprises: a first pin isolation valve, the first pin isolation valve disposed to move along the axis of rotation of the isolation valve, the first pin isolation valve movably disposed so as to be capable of fluidically communicating with the at least one blank opening on the first of the at least two opposing surfaces, and movably disposed so as to be capable of fluidically communicating with the flow through conduit having an opening on the outer surface and an opening on a second of the at least two opposing surfaces; and a second pin isolation valve, the second pin isolation valve disposed to move along the centerline of the isolation valve, the second pin isolation valve movably disposed so as to be capable of fluidically communicating with the at least one blank opening on the second of the at least two opposing surfaces, the second pin isolation valve movably disposed so as to be capable of fluidically communicating with the flow through conduit having an opening on the outer surface and an opening on the second of the at least two opposing surfaces. The multiple valve further comprises: a linear flow through injection valve, the injection valve comprising: a stationary member; a movable member, the stationary member and the movable member interfacing at a surface, the movable member disposed to slide along the surface; a chamber disposed between the stationary member and the movable member, the chamber bounded by the surface; the movable member having a first flow through conduit having a first opening interfacing with the chamber and a second opening on a surface of the movable member not interfacing with the chamber, the movable member having a second flow through conduit having a first opening interfacing with the chamber and a second opening on a surface of the movable member not interfacing with the chamber. The movable member further comprises: a third flow through conduit having a first opening and a second opening each on a surface of the movable member interfacing with the chamber; and a fourth flow through conduit having a first opening and a second opening each on a surface of the movable member interfacing with the chamber.

In yet another embodiment, the present invention is directed to a multiple valve comprised of: a housing; a linear flow through isolation valve disposed within the housing, the isolation valve comprising: a stationary member; a movable member, the stationary member and the movable member interfacing at a surface, the movable member disposed to slide along the surface; a chamber disposed between the stationary member and the movable member, with the chamber bounded by the surface. The movable member has a first flow through conduit having an opening interfacing with the chamber and an opening on a surface of the movable member not interfacing with the chamber, a second flow through conduit having an opening interfacing with the chamber, and an opening on a surface of the movable member not interfacing with the chamber, a first blank opening on the surface bounding the chamber, and a second blank opening on the surface bounding the chamber. The multiple valve further comprises a linear flow through injection valve, the injection valve comprising: a stationary member; a movable member, the stationary member and the movable member interfacing at a surface, the movable member disposed to slide along the surface; and a chamber disposed between the stationary member and the movable member, the chamber bounded by the surface. The movable member has: a first flow through conduit having a first opening interfacing with the chamber and a second opening on a surface of the movable member not interfacing with the chamber, a second flow through conduit having a first opening interfacing with the chamber and a second opening on a surface of the movable member not interfacing with the chamber, a third flow through conduit having a first opening and a second opening each on a surface of the movable member interfacing with the chamber, and a fourth flow through conduit having a first opening and a second opening each on a surface of the movable member interfacing with the chamber.

The linear flow through injection valve of the multiple valve can further comprise: at least one of a (a) first pin isolation valve, (b) second pin isolation valve, (c) third pin isolation valve, and (d) fourth pin isolation valve; the first pin isolation valve having an internal conduit, the first pin isolation valve disposed within an opening within the stationary member interfacing with the chamber so that the internal conduit of the first pin isolation valve is movably disposed to be in fluidic communication with the first opening on a first flow through conduit of the movable member, and movably disposed to be in fluidic communication with the first opening of the third flow through conduit, the second pin isolation valve having an internal conduit, the second pin isolation valve disposed within an opening within the stationary member interfacing with the chamber so that the internal conduit of the second pin isolation valve is movably disposed to be in fluidic communication with the first opening on a second flow through conduit of the movable member, and movably disposed to be in fluidic communication with the second opening of the third flow through conduit, the third pin isolation valve having an internal conduit, the third pin isolation valve disposed within an opening within the stationary member interfacing with the chamber so that the internal conduit of the third pin isolation valve is movably disposed to be in fluidic communication with the first opening of the fourth flow through conduit, and movably disposed to be in fluidic communication with the first opening of the first flow through conduit. The fourth pin isolation valve has an internal conduit, the fourth pin isolation valve disposed within an opening within the stationary member interfacing with the chamber so that the internal conduit of the fourth pin isolation valve is movably disposed to be in fluidic communication with the second opening of the fourth flow through conduit, and movably disposed to be in fluidic communication with the first opening of the second flow through conduit.

Those skilled in the art recognize that any combination such as rotary isolation and linear injection, linear isolation and rotary injection, rotary injection and rotary isolation, and linear injection and linear isolation multiple valves can be constructed. Furthermore, any of the rotary injection, rotary isolation, linear injection, and linear isolation valves can be constructed independently.

The present invention is also directed to a method of operating a flow through injection valve, the valve comprising: a movable member, the movable member having first and second conduits for interfacing with internal conduits of first and second pin isolation valves, the first and second conduits opening to a surface of the movable member; a third conduit enabling fluidic communication between the internal conduits of the first and second pin isolation valves; a fourth conduit enabling fluidic communication between internal conduits of third and fourth pin isolation valves, the third pin isolation valve providing fluid flow, the fourth pin isolation valve exhausting the fluid flow;

(A) wherein the valve is in an initial position of flow isolation such that the third pin isolation valve providing fluid flow is in fluidic communication with the fourth pin isolation valve exhausting the fluid flow, the first pin isolation valve is in fluidic communication with the first conduit, and the second pin isolation valve is in fluidic communication with the second conduit; the method comprises the steps of: (I) wherein the first pin isolation valve interfaces with the first conduit, (1) moving the first pin isolation valve away from the first conduit; (2) moving the movable member, (3) moving the first pin isolation valve towards the movable member such that the internal conduit within the first pin isolation valve interfaces with the third conduit; and (II) wherein the second pin isolation valve interfaces with the second conduit, (1) moving the second pin isolation valve away from the second conduit; (2) moving the movable member, (3) moving the second pin isolation valve towards the movable member such that the internal conduit within the second pin isolation valve interfaces with the third conduit, thereby establishing fluidic communication between the first and second pin isolation valves; and (III) wherein the third pin isolation valve interfaces with the fourth conduit, (1) moving the third pin isolation valve away from the fourth conduit; (2) moving the movable member; (3) moving the third pin isolation valve towards the first conduit to establish fluidic communication with the internal conduit of the third pin isolation valve; and (IV) wherein the fourth pin isolation valve interfaces with the fourth conduit, (1) moving the fourth pin isolation valve away from the fourth conduit; (2) moving the movable member; (3) moving the fourth pin isolation valve towards the second conduit to establish fluidic communication with the internal conduit of the fourth pin isolation valve; and (B) wherein the valve is in an initial position of flow throughput such that at least one of (a) the third pin isolation valve providing fluid flow interfaces with the first conduit and (b) the fourth pin isolation valve exhausting the fluid flow interfaces with the second conduit, the method comprises the steps of: (III) wherein the third pin isolation valve interfaces with the first conduit, (1) moving the third pin isolation valve away from the first conduit, (2) moving the movable member, and (3) moving the third pin isolation valve towards the movable member such that the internal conduit within the third pin isolation valve interfaces with the fourth conduit; and (IV) wherein the fourth pin isolation valve interfaces with the second conduit, (1) moving the fourth pin isolation valve away from the second conduit, (2) moving the movable member, and (3) moving the fourth pin isolation valve towards the movable member such that the internal conduit within the second pin isolation valve interfaces with the first conduit; and (V) wherein the first pin isolation valve interfaces with the third conduit, (1) moving the first pin isolation valve away from said third conduit, (2) moving the movable member, and (3) moving the first pin isolation valve towards the movable member such that the internal conduit within the first pin isolation valve interfaces with the first conduit; and (VI) wherein the second pin isolation valve interfaces with the third conduit, (1) moving the second pin isolation valve away from the third conduit, (2) moving the movable member, and (3) moving the second pin isolation valve towards the movable member such that the internal conduit within the second pin isolation valve interfaces with the second conduit.

In another embodiment of the present invention, the present invention is directed also to a method of operating a multiple valve, the multiple valve comprising a flow through isolation valve, the flow through isolation valve comprising: a movable member, the movable member having first and second conduits for interfacing with internal conduits of first and second pin isolation valves, the conduits opening to a surface of the movable member; first and second blank openings for interfacing with the internal conduits of the first and second pin isolation valves, (A) wherein the valve is in an initial position of flow isolation such that at least one of (a) the first pin isolation valve providing fluid flow interfaces with the first blank opening and (b) the second pin isolation valve exhausting the fluid flow interfaces with the second blank opening, the method comprises the steps of: (I) wherein the first pin isolation valve interfaces with the first blank opening, (1) moving the first pin isolation valve away from the first blank opening, (2) moving the movable member, and (3) moving the first pin isolation valve towards the movable member such that the internal conduit within the first pin isolation valve interfaces with the first conduit opening to a surface of the movable member; and (II) wherein the second pin isolation valve interfaces with the second blank opening, (1) moving the second pin isolation valve away from the second blank opening, (2) moving the movable member, and (3) moving the second pin isolation valve towards the movable member such that the internal conduit within the second pin isolation valve interfaces with the second conduit opening to a surface of the movable member, and (B) wherein the valve is in an initial position of flow throughput such that at least one of (a) the first pin isolation valve providing fluid flow interfaces with the first conduit and (b) the second pin isolation valve exhausting the fluid flow interfaces with the second conduit, the method comprises the steps of: (III) wherein the first pin isolation valve interfaces with the first conduit, (1) moving the first pin isolation valve away from the first conduit, (2) moving said movable member, and (3) moving the first pin isolation valve towards the movable member such that the internal conduit within the first pin isolation valve interfaces with the first blank opening; and (IV) wherein the second pin isolation valve interfaces with the second conduit, (1) moving the second pin isolation valve away from the second conduit, (2) moving the movable member, and (3) moving the second pin isolation valve towards the movable member such that the internal conduit within the second pin isolation valve interfaces with the second blank opening.

In the method of operating a flow through injection valve, the first and second conduits opening to a surface of the movable member can be in fluidic communication with a sample loop of a high pressure liquid chromatography (HPLC) system, or the first and second pin isolation valves can be in fluidic communication with a needle and a syringe of a high pressure liquid chromatography (HPLC) system, or the third and fourth pin isolation valves can be in fluidic communication with a pump and a column of a high pressure liquid chromatography (HPLC) system, In the method of operating a multiple valve, the multiple valve also comprises a flow through injection valve, the flow through injection valve comprising: a movable member, the movable member having first and second conduits for interfacing with internal conduits of first and second pin isolation valves, the first and second conduits opening to a surface of the movable member; a third conduit enabling fluidic communication between the internal conduits of the first and second pin isolation valves; a fourth conduit enabling fluidic communication between internal conduits of third and fourth pin isolation valves, the third pin isolation valve providing fluid flow, the fourth pin isolation valve exhausting the fluid flow; (A) wherein the valve is in an initial position of flow isolation such that the third pin isolation valve providing fluid flow is in fluidic communication with the fourth pin isolation valve exhausting the fluid flow, the first pin isolation valve is in fluidic communication with the first conduit, and the second pin isolation valve is in fluidic communication with the second conduit; the method comprises the steps of: (I) wherein the first pin isolation valve interfaces with the first conduit, (1) moving the first pin isolation valve away from the first conduit; (2) moving the movable member, (3) moving the first pin isolation valve towards the movable member such that the internal conduit within the first pin isolation valve interfaces with the third conduit; and (II) wherein the second pin isolation valve interfaces with the second conduit, (1) moving the second pin isolation valve away from the second conduit; (2) moving the movable member, (3) moving the second pin isolation valve towards the movable member such that the internal conduit with the second pin isolation valve interfaces with the third conduit, thereby establishing fluidic communication between the first and second pin isolation valves; and (III) wherein the third pin isolation valve interfaces with said fourth conduit, (1) moving the third pin isolation valve away from the fourth conduit; (2) moving the movable member;

(3) moving the third pin isolation valve towards the first conduit to establish fluidic communication with the internal conduit of the third pin isolation valve; and (IV) wherein said fourth pin isolation valve interfaces with the fourth conduit, (1) moving the fourth pin isolation valve away from the fourth conduit; (2) moving the movable member; (3) moving the fourth pin isolation valve towards the second conduit to establish fluidic communication with the internal conduit of the fourth pin isolation valve.

The method of operating a multiple valve also comprises the steps of: (B) wherein the valve is in an initial position of flow throughput such that at least one of (a) the third pin isolation valve providing fluid flow interfaces with the first conduit and (b) the fourth pin isolation valve exhausting the fluid flow interfaces with the second conduit, the method comprises the steps of: (III) wherein the third pin isolation valve interfaces with the first conduit, (1) moving the third pin isolation valve away from the first conduit, (2) moving the movable member, and (3) moving the third pin isolation valve towards the movable member such that the internal conduit within the third pin isolation valve interfaces with the fourth conduit; and (IV) wherein the fourth pin isolation valve interfaces with the second conduit, (1) moving the fourth pin isolation valve away from the second conduit, (2) moving the movable member, and (3) moving the fourth pin isolation valve towards the movable member such that the internal conduit within the second pin isolation valve interfaces with the first conduit; and (V) wherein the first pin isolation valve interfaces with the third conduit, (1) moving the first pin isolation valve away from the third conduit, (2) moving the movable member, and (3) moving the first pin isolation valve towards the movable member such that the internal conduit within the first pin isolation valve interfaces with the first conduit; and (VI) wherein the second pin isolation valve interfaces with the third conduit, (1) moving the second pin isolation valve away from the third conduit, (2) moving the movable member, and (3) moving the second pin isolation valve towards the movable member such that the internal conduit within the second pin isolation valve interfaces with the second conduit.

In the method of operating a multiple valve, the first and second conduits opening to a surface of the movable member of the flow through injection valve can be in fluidic communication with a sample loop of a high pressure liquid chromatography (HPLC) system, or the first and second pin isolation valves of the flow through injection valve are in fluidic communication with a needle and a syringe of a high pressure liquid chromatography (HPLC) system, or the third and fourth pin isolation valves of the flow through injection valve can be in fluidic communication with a pump and a column of a high pressure liquid chromatography (HPLC) system,

BRIEF DESCRIPTION OF THE DRAWINGS

These and other features, benefits and advantages of the present invention will become apparent by reference to the following text and figures, with like reference numbers referring to like structures across the views, wherein.

DETAILED DESCRIPTION OF THE INVENTION

This application incorporates by reference concurrently filed provisional application Ser. No. 60/550,923.

The present invention describes a combination isolation valve of multiple flow-through high pressure isolation valves for high pressure fluids. The combination isolation valve can replace the conventional face shear valve used in HPLC systems. The rotors are designed for use in high pressure fluid systems to permit switching to another flow path without temporarily blocking flow as would occur in face-shear valves as are customarily used in high pressure fluid systems, in particular in high pressure liquid chromatography. The sample fluid injection circuit may be isolated from the remainder of the HPLC system. Each of the combination multiple flow-through isolation valves include a housing having a bore there through and a cylindrical rotor rotatable within the bore.

When the isolate rotor is in its fluid flow position during the injection phase, fluid flows from a pump, through the isolation valve, to the sample injector circuit, back through another portion of the valve, and then to a column. By turning the rotor 90°, the fluid stop ports prevent the flow of fluid and isolate the sample circuit from the remainder of the HPLC system.

Figure 1A:
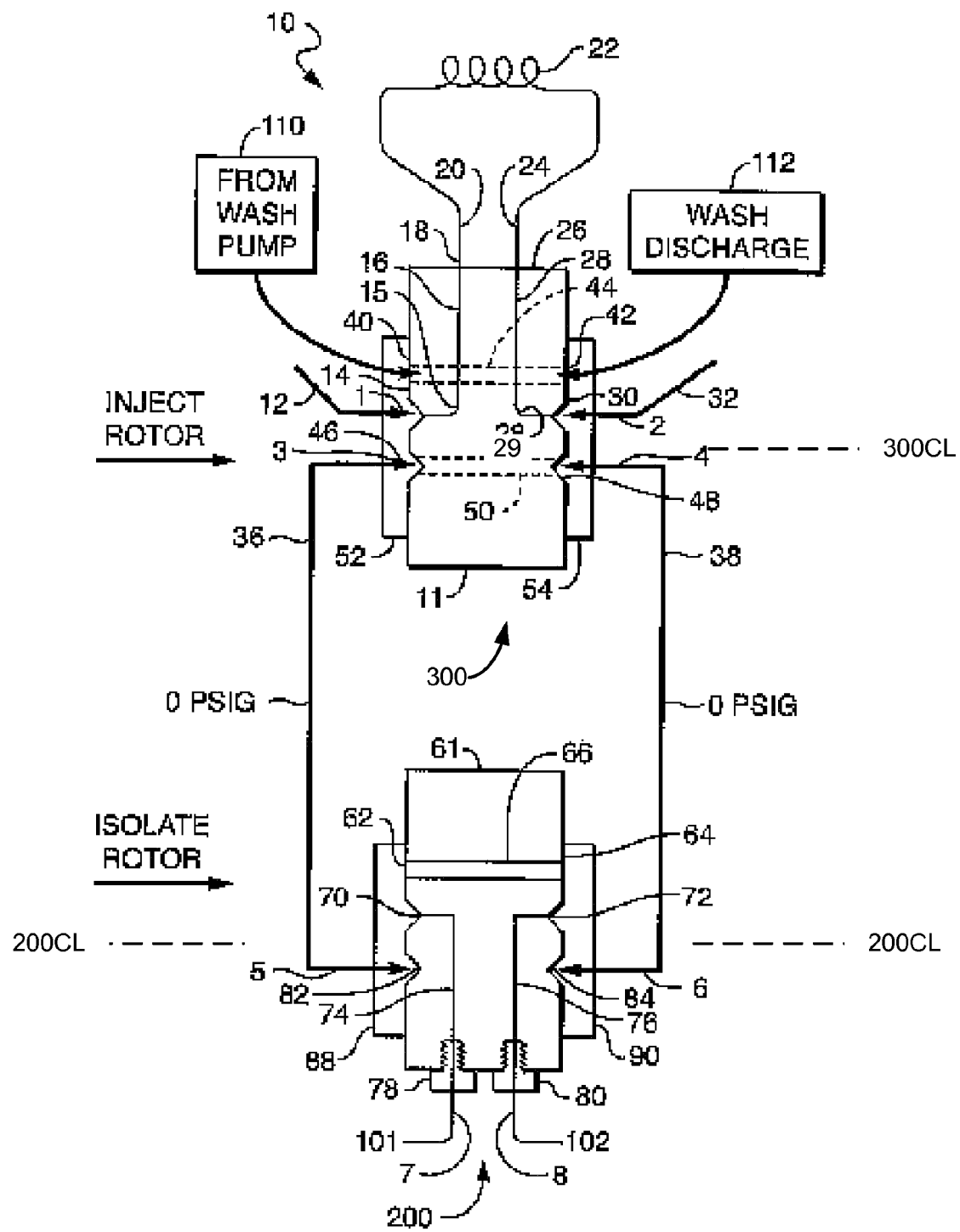
FIG. 1A illustrates a combination of multiple rotary flow-through isolation valves of the present invention in a side elevation cross-sectional view in the load position interfacing with a sample loop.

In particular, in FIG. 1A, an inject rotor 11 of an injection valve 300 of combination or multiple isolation valve 10 is shown in a load phase in fluidic communication with a needle 12 to a pin valve 1 at a port 14 on a side of rotor 11. The combination or multiple isolation valve 10 is comprised of an isolation valve 200 and the injection valve 300. Sample fluid flows from the pin valve 1 into internal conduit 16. The sample fluid flows through typically a substantially 90 degree bend 15 to a port 18 on the outer surface of the rotor 11. The port 18 is preferably fluidically coupled to an inlet flexible tube 20 and correspondingly to the sample loop 22 so that the sample fluid flows into the sample loop 22 and flows out through an outlet flexible tube 24.

The outlet flexible tube 24 is preferably fluidically coupled to a port 26 that is on the outer surface of rotor 11 through a pin valve 2 and in turn to an internal conduit 28. The sample fluid flows through typically a substantially 90 degree bend 29 to a port 30 on an opposite side of the rotor 11. A syringe 32 can be fluidically coupled to the port 30 so as to provide negative pressure in the flexible tube 24, sample loop 22, flexible tube 20 and needle 12 for drawing up the sample fluid and to permit the sample fluid to be aspirated into the sample loop 22.

The inject rotor 11 includes ports 40 and 42 which interface through internal channel 44; and ports 46 and 48 which interface through internal channel 50. An annular space 52 is formed on one side of the rotor 11 providing fluidic communication between ports 14, 40 and 46. An annular space 54 is formed on the opposite side of the rotor 11 providing fluidic communication between ports 30, 42 and 48.

During the load phase, the inject rotor 11 is isolated from the high pressure pump 101 and column 102 by means of an isolation rotor 61. The two rotors 11 and 61 interface through high pressure tubing 36 and 38. In particular, high pressure tubing 36 is fluidically coupled with internal channel 50 through pin valve 3 at port 46 while high pressure tubing 38 is fluidically coupled to internal channel 50 through pin valve 4. The high pressure tubing 36 is fluidically coupled to isolate rotor 61 through pin valve 5 which interfaces with the rotor 61 at blank port 82. Correspondingly, the high pressure tubing 38 is fluidically coupled to isolation rotor 61 through pin valve 6 which interfaces with the rotor 61 at blank port 84. Therefore, during the load phase, the pressure within the high pressure tubing 36 and 38 is substantially atmospheric, i.e., 0 psig or 0.101 MPa absolute.

The isolation rotor 61 includes ports 62 and 64 which interface through internal channel 66. High pressure pump 101 is fluidically coupled to port 70 by means of internal channel 74. The pump 101 interfaces with the outer surface of rotor 61 at a port 78. Similarly, column 102 is fluidically coupled to port 72 by means of internal channel 76. The column 102 interfaces with the outer surface of rotor 61 at a port 80.

The inject rotor 11 can include a wash pump interfacing at port 40 and a wash discharge interfacing at port 42. Since stagnant flow can occur in the internal rotor passageway 44, rotor wash supply connection 110 is provided to connect from a separate wash pump (not shown) while wash discharge connection 112 enables discharge of the used wash solution.

The wash pump washes the internal chamber 44 following sample injection. An annular space 88 is formed on one side of the rotor 61 providing fluidic communication between ports 62 and 70. An annular space 90 is formed on the opposite side of the rotor 61 providing fluidic communication between ports 64 and 72.

Figure 1B:
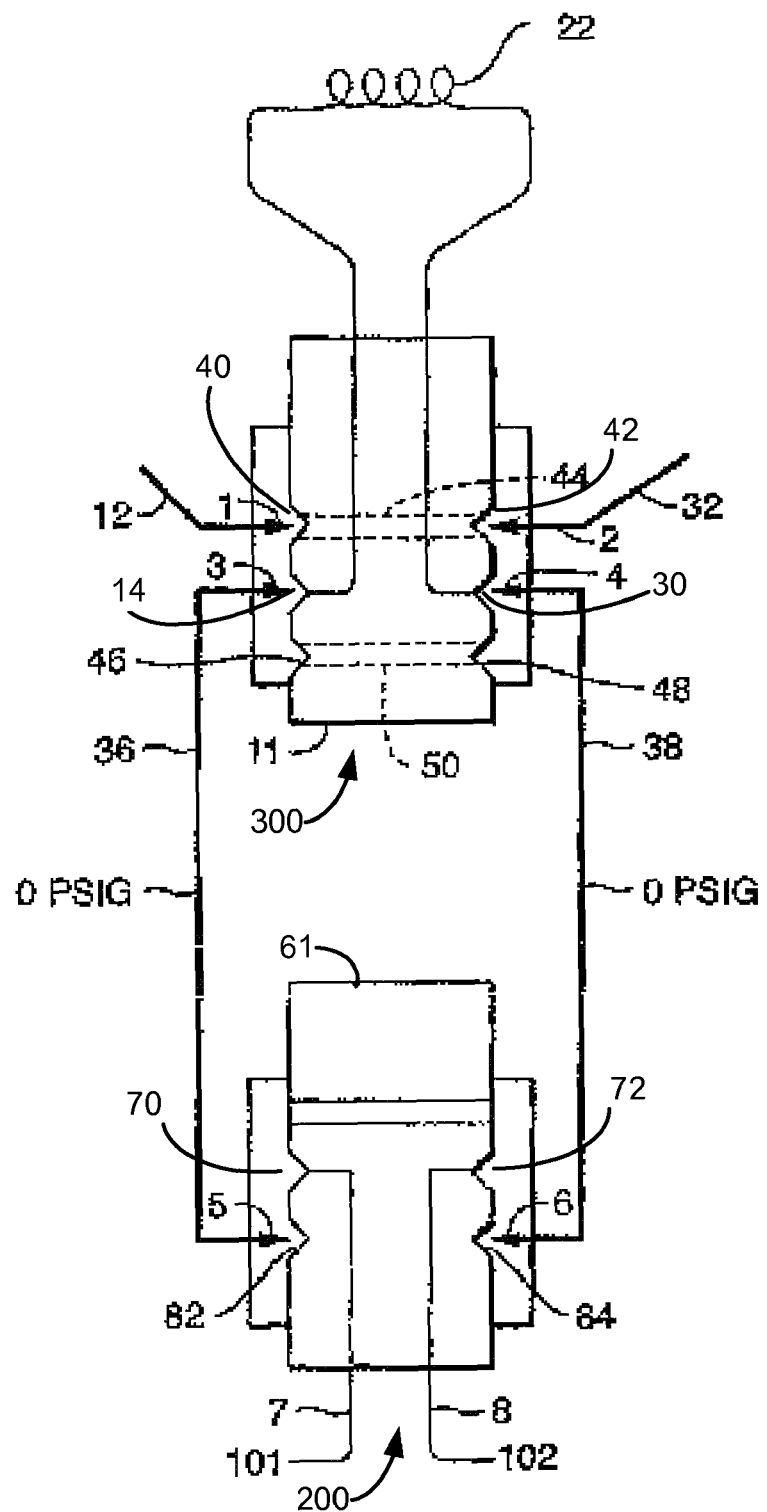
FIG. 1B illustrates the combination of multiple flow-through rotary isolation valves of the present invention of FIG. 1A in a transition position interfacing with a sample loop.

FIG. 1B illustrates the transition phase between loading of the sample into the sample loop 22 and the injection phase where the sample within the loop 22 is injected by high pressure pump 101. During the transition phase, the isolation rotor 61 remains in the same position as during the load phase. Only orientation of the inject rotor 11 is changed. Specifically, the rotor 11 is rotated so that the pin valves 1 and 2 are disconnected from the sample loop 22, thereby isolating the needle 12 and the syringe tube 32 from the sample loop 22. The pin valve 1 is inserted into port 40 while the pin valve 2 is inserted into port 42 so that the needle and syringe are fluidically coupled to each other through internal conduit 44.

Figure 1C:
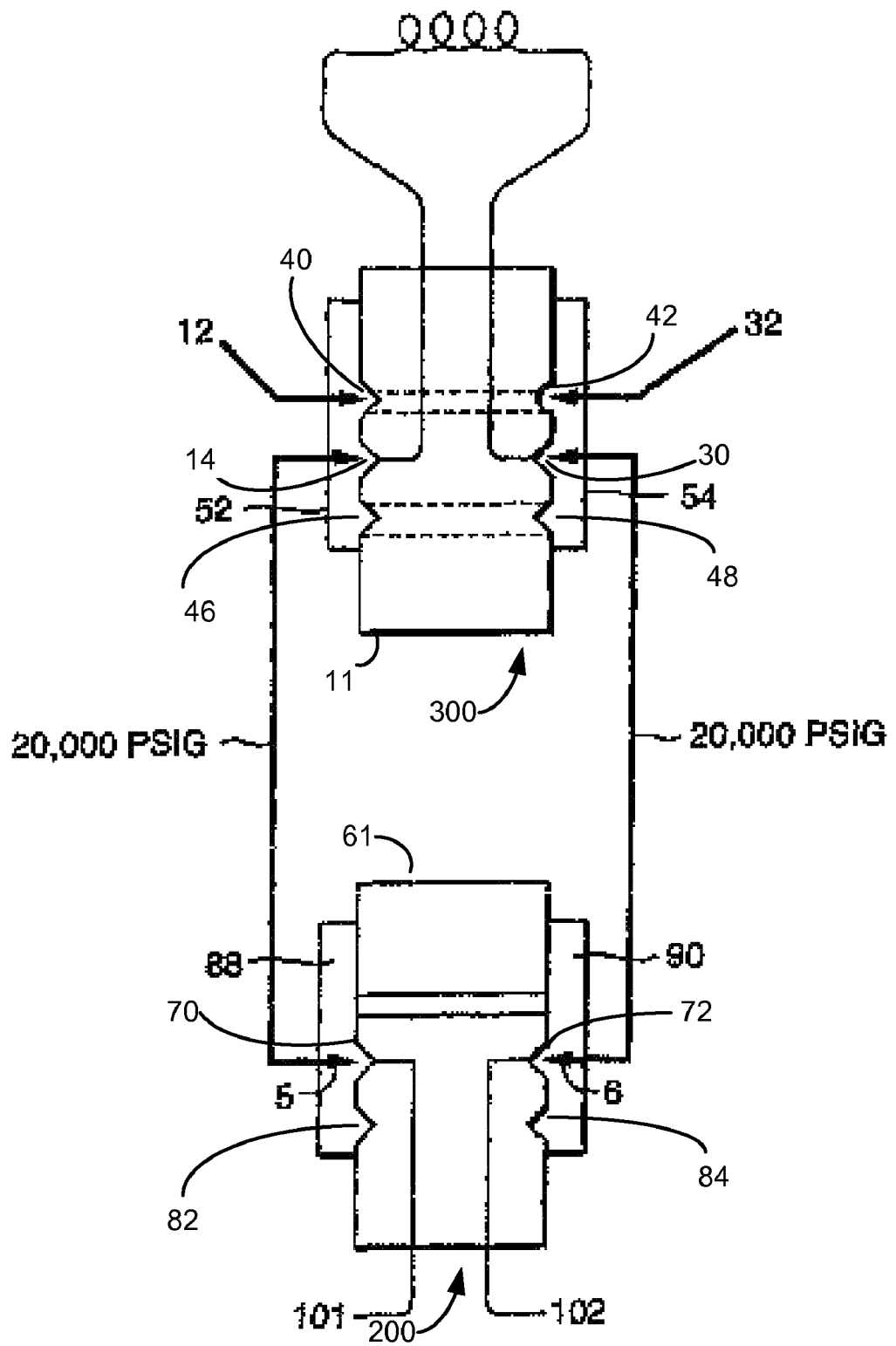
FIG. 1C illustrates the combination of multiple flow-through rotary isolation valves of the present invention of FIG. 1A in an injection position interfacing with a sample loop.

FIG. 1C illustrates the injection phase when high pressure liquid is supplied from the pump 101 to sample loop 22 and on to the column 102. Specifically, in the injection phase, the rotor 11 remains in the position achieved during the transition phase. The rotor 61 is rotated so that the valve pin valves 5 and 6 are disconnected from the blank ports 82 and 84, respectively. The pin valve 5 is now connected to port 70 so as to cause fluidic communication between the pump 101 and the high pressure tubing 36. Correspondingly, the pin valve 6 is now connected to port 72 so as to cause fluidic communication between the high pressure tubing 38 and the column 102.

The annular spaces 88 and 90 formed on opposite sides of the rotor 61 provide a high pressure seal annulus for the rotor 61.

Those skilled in the art recognize that following the inject phase illustrated in FIG. 1C, the flow through isolation valve 200 and the flow through injection valve 300 can be returned to the load phase by reversing the operation back to the transition phase illustrated in FIG. 1B and subsequently to the load phase illustrated in FIG. 1A.

Figure 2A:
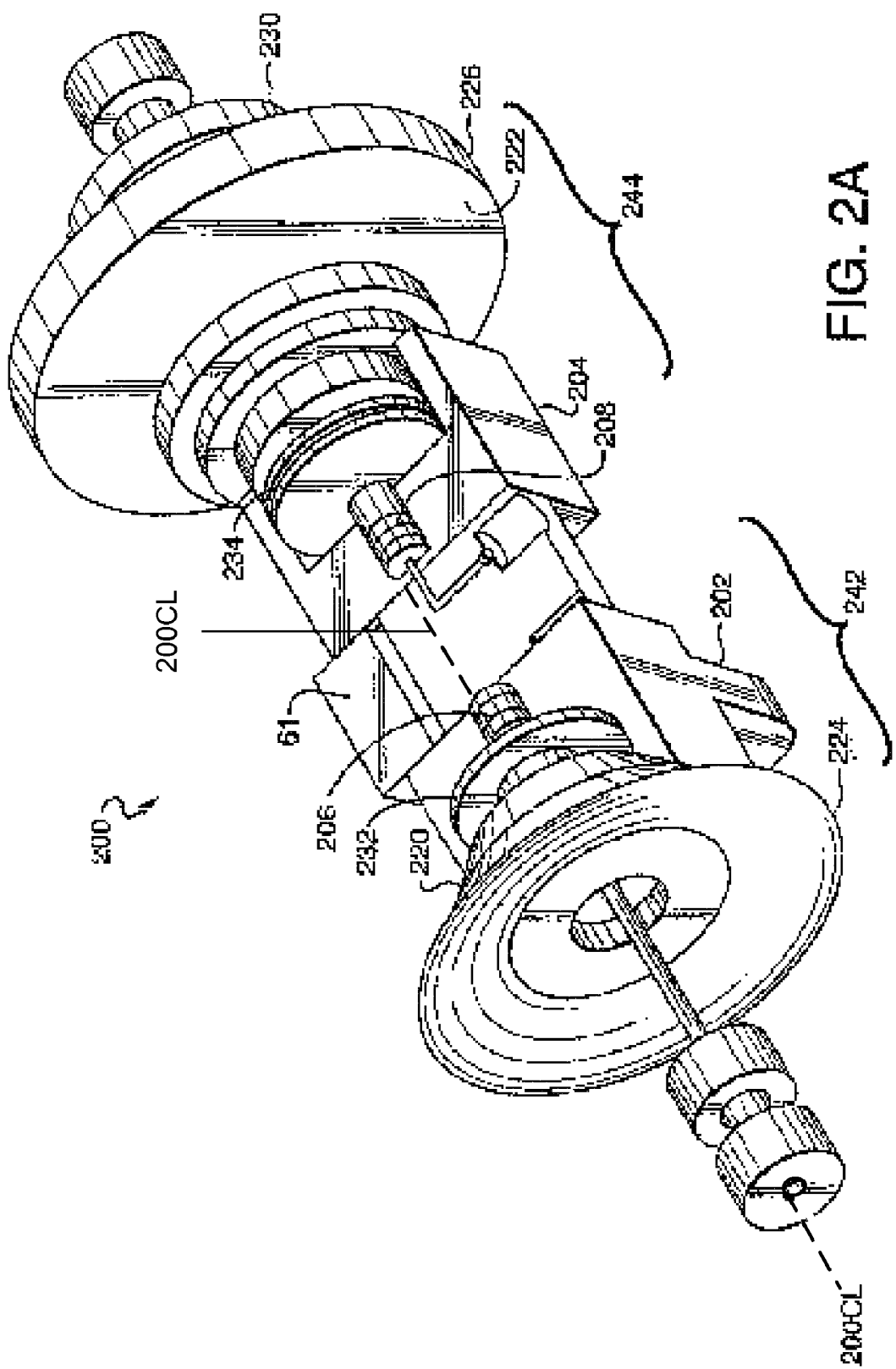
FIG. 2A is a partial cut-away perspective view of the isolation portion of the combination of the multiple flow-through rotary isolation valves of FIGS. 1A-1C.

FIG. 2A illustrates a perspective view of the isolation rotor 61 as it is disposed within a valve body to form a valve assembly 200. The components of valve assembly 200 typically are centered around an axis of rotation such as centerline 200CL. Specifically, the rotor 61 is positioned so that stators 202 and 204 are disposed on either end of the rotor 61. Belleville springs 220 and 222 deflect the axial loads along the centerline 200CL which act on the rotor 61. The Belleville springs 220 and 222 and Belleville washers 232 and 234 are mounted on an end of both stators 202 and 204 by means of flanges 224 and 226. The load washers 224 and 226 are locked into position by spherical nuts 228 and 230. Both sets of sealing layers 206 and 208 are compressed by the axial forces imposed by Belleville spring washers 232 and 234, respectively. The rotor 61 is comprised preferably of PEEK (polyetheretherketone) or PEEK blend. The rotor clamp 240 and the stators 202 and 204 are comprised preferably of Type 316 stainless steel The foregoing materials are not exclusive and other materials can be applied by those skilled in the art.

The rotor 61 is shown in a cutaway view disposed between stators 202 and 204. The rotor 61 is sealed by a set of three sealing layers 206 and 208 set around the pin valves 5 and 6, respectively. The preferred materials for the sealing layers 206 and 208 comprise PEEK, PTFE (polytetrafluoroethylene), PEEK in that order.

The foregoing materials are not exclusive and other materials can be applied by those skilled in the art.

The respective ends 242 and 244 of the flow through isolation valve 200 can be considered to comprise the stators 202 and 204, the sealing layers 206 and 208, Belleville spring washers 232 and 234, Belleville springs 220 and 222, load washers 224 and 226 and spherical nuts 228 and 230.

Figure 2B:
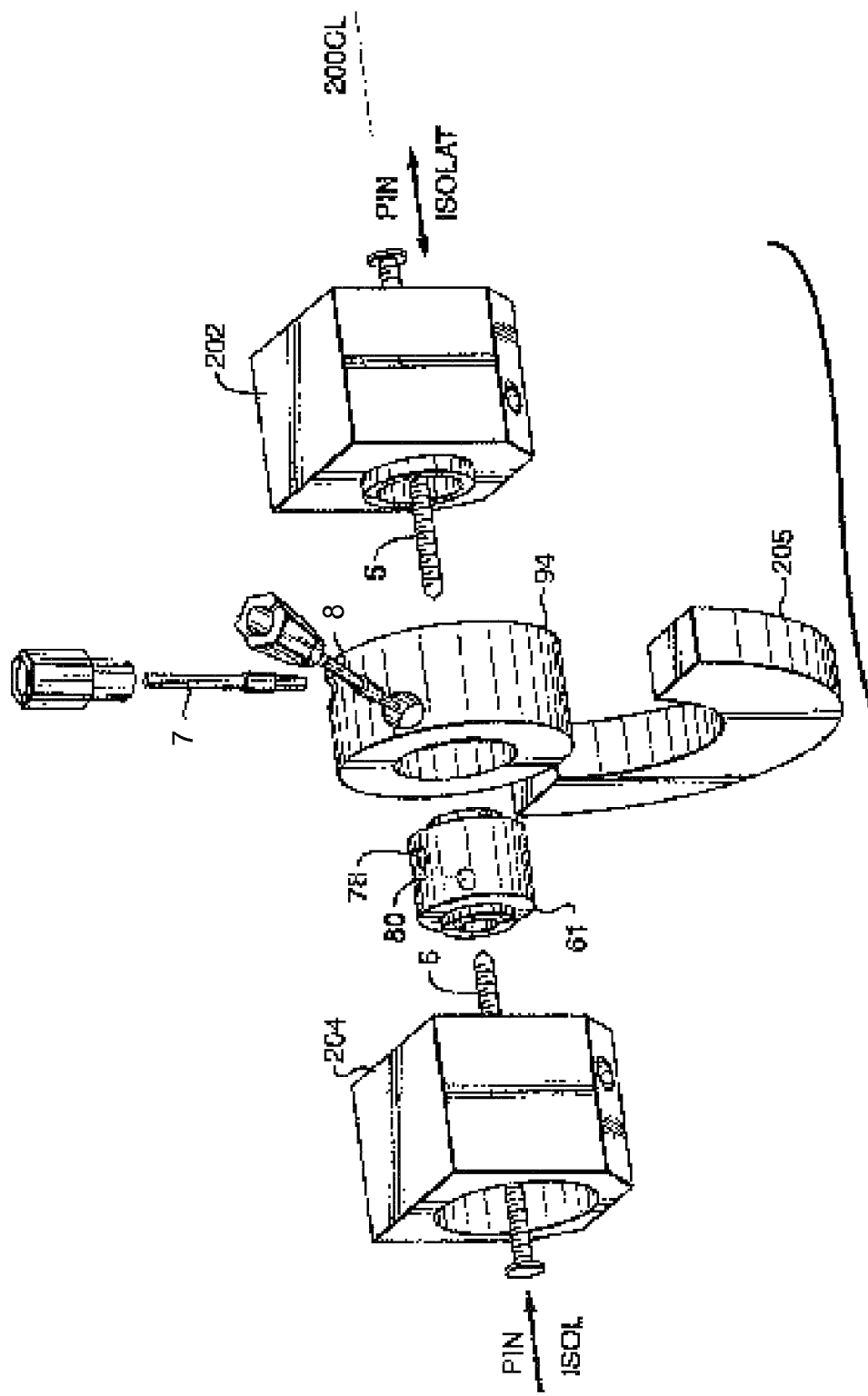
FIG. 2B is a perspective exploded view of the rotor of the isolation portion of the multiple flow-through rotary isolation valve of FIGS. 1A-1C.

FIG. 2B is an exploded view of a portion of the components comprising a first variation of the embodiment of the flow through isolation valve 200. Pump supply fitting 7 interfaces with port 78 in the rotor 61 and outlet supply to column fitting 8 interfaces with port 80 in the rotor 61. Face seal valve supply pin 6 (not shown) is surrounded by stator 204 and interfaces with one end of the rotor 61 while face seal valve discharge pin 5 (not shown) is surrounded by stator 202 and interfaces with the opposite end of the rotor 61. During normal operation, only the pins 5 and 6 which are surrounded by the stators 202 and 204 are moved either away from or back towards the rotor 61. The pump supply fitting 7 and outlet supply to column fitting 8 are maintained normally in position except that they are rotated together with the rotation of the rotor 61. The rotor 61 and rotor clamp 94 are rotated around the centerline 200CL by means of drive gear 205.

When the rotor 61 is in its fluid flow position, fluid flows from a separate high pressure pump, through the isolation valve 200, to the sample injector circuit of injection valve 10, back to the isolation valve 200, and then to a column.

When the rotor 61 is rotated around axis of rotation centerline 200CL by means of drive gear 205 through an angle of preferably 90°, the pins 5 and 6 are repositioned to the blank fluid flow stop ports 82 and 84 which prevent the flow of fluid and isolate the sample circuit of injection valve 10 from the remainder of the HPLC system. Those skilled in the art recognize that the drive gear 205 can be either a separate unit from the rotor clamp 94 or else the drive gear 205 can be an integral unitary structure combined with the rotor clamp 94 and even the rotor 61. In addition, although shown as a drive gear, other means known to those skilled in the art such as, for example, an operating handle can be employed.

Although the ports 78 and 80 are preferably offset by an angle of about 90° from each other on the outer surface of the rotor, the ports can be aligned to be adjacent to each other. The offset is preferred due to the advantage of threaded connections for sealing and the resultant need for larger diameter tap holes. The threaded tap holes are generally 7.9 mm (5/16 in.) in diameter.

Figure 3A:
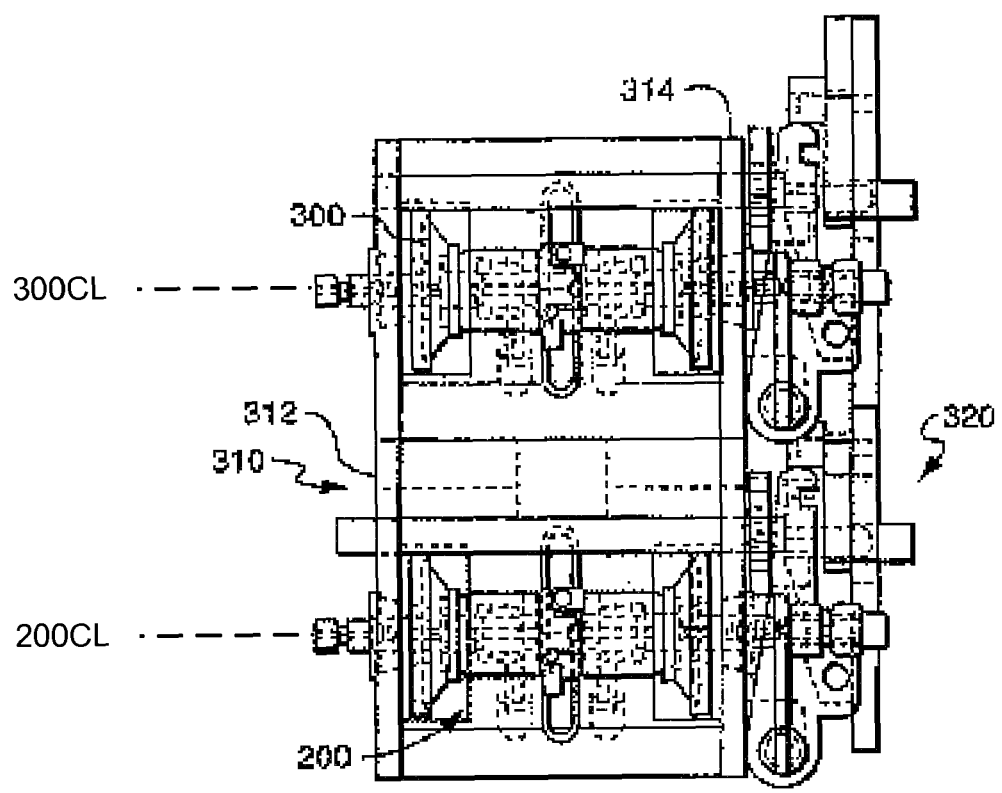
FIG. 3A is a plan view of the housing of the multiple rotary flow-through isolation valves of FIGS. 1A-1C.
Figure 3B:
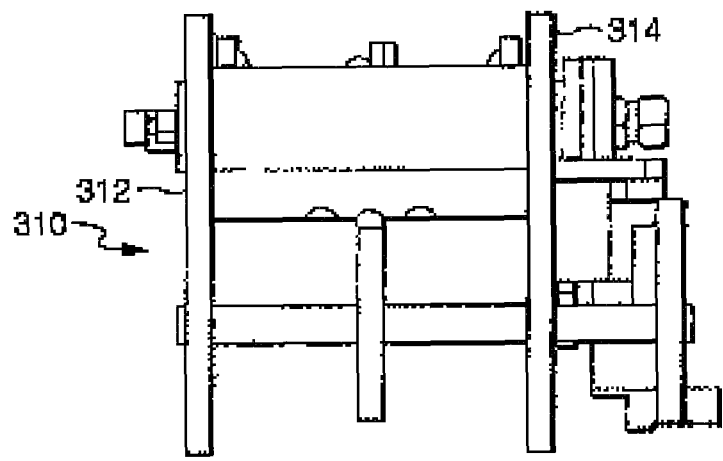
FIG. 3B is an elevation view of the housing of the multiple flow-through rotary isolation valves of FIGS. 1A-1C.

FIG. 3A is a plan view of the housing 310 of the multiple flow-through isolation valves of FIGS. 1A-1C. FIG. 3B is an elevation view of the housing of the multiple flow-through isolation valves of FIGS. 1A-1C.

The isolation valve assembly 200 is disposed within the housing 310. The injection rotor 11 is disposed within injection valve assembly 300 around an axis of rotation such as centerline 300CL. The isolation valve assembly 200 and the injection valve assembly 300 are disposed within the housing 310 through the end plates 312 and 314 preferably such that the axis of rotation centerlines 200CL and 300CL are parallel to each other. The valve assemblies 200 and 300 are operated by means such as a cam mechanism 320 known to those skilled in the art.

Figure 3D:
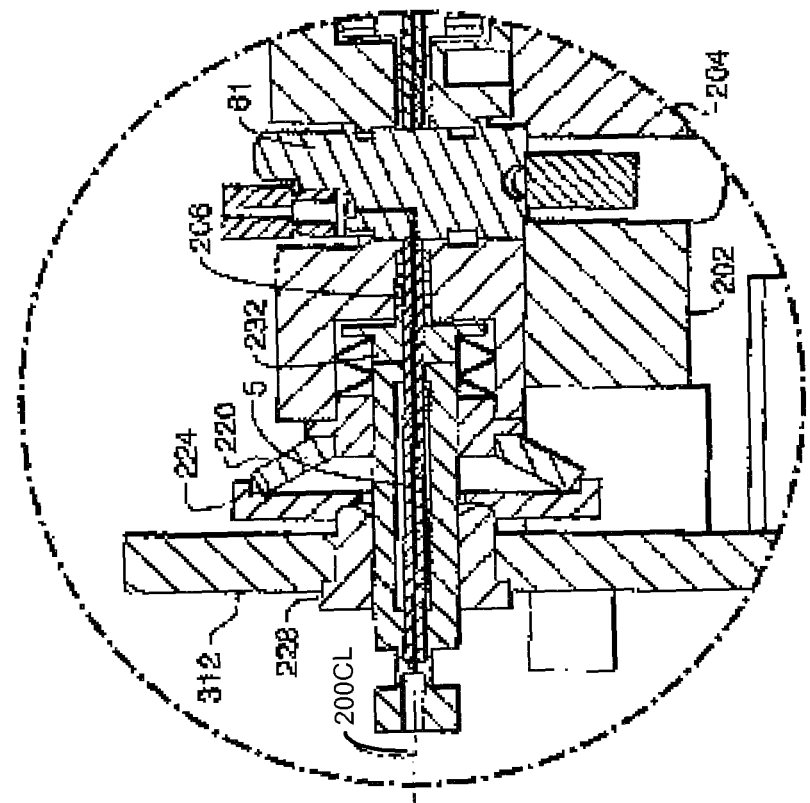
FIG. 3C and FIG. 3D are detail views of a portion of the rotary isolation valve assembly of FIG. 3A.
Figure 3C:
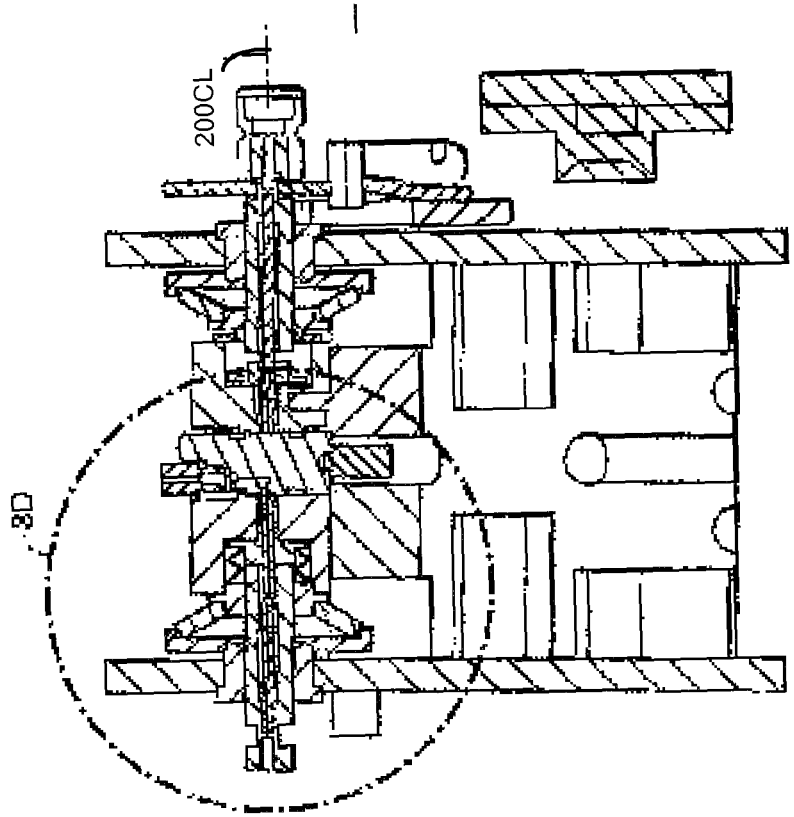

FIG. 3C and FIG. 3D are detail views of a portion of the isolation valve assembly of FIG. 3A. As before, the rotor 61 is positioned so that stators 202 and 204 are disposed on either end of the rotor 61. Belleville springs 220 and 222 deflect the axial loads along the centerline 200CL which act on the rotor 61. The Belleville spring 220 is mounted on an end of stator 202 by means of load washer 224. The load washer 224 is locked into position by spherical nut 228. Sealing layer set 206 is compressed by the axial force imposed by Belleville spring washer 232. The spherical nuts 228 and 230 (not shown) are supported by, and penetrate through, housing end plates 312 and 314, respectively.

As described previously with respect to FIG. 2A, the rotor 61 is shown in a cutaway view in FIG. 3C disposed between stators 202 and 204. The rotor 61 is sealed by a set of three sealing layers 206 and 208 set around the pin valves 5 and 6, respectively. As previously noted, the preferred materials and arrangement for the sealing layers comprise PEEK, PTFE, PEEK in that order. A valve end 240 of the flow through isolation valve assembly 200 can be considered to comprise the stator 202, the sealing layer 206, Belleville spring washer 232, Belleville spring 220, load washer 224, and spherical nut 228. Those skilled in the art recognize that the opposite valve end of the isolation valve assembly 200 is typically symmetrical and therefore is comprised typically of the corresponding symmetrical components.

In addition, those skilled in the art recognize that the isolation valve 200 and injection valve 300 of combination isolation valve 10 can also be configured by either of the alternate embodiments in any combination of embodiments described in U.S. Provisional Patent Application No. 60/550,923, previously disclosed as being incorporated by reference. That is, either the first and second embodiments, or the first and third embodiments, or the second and third embodiments, or only the second embodiment or only the third embodiment can be applied correspondingly as isolation valve 200 and injection valve 300.

Figure 4A:
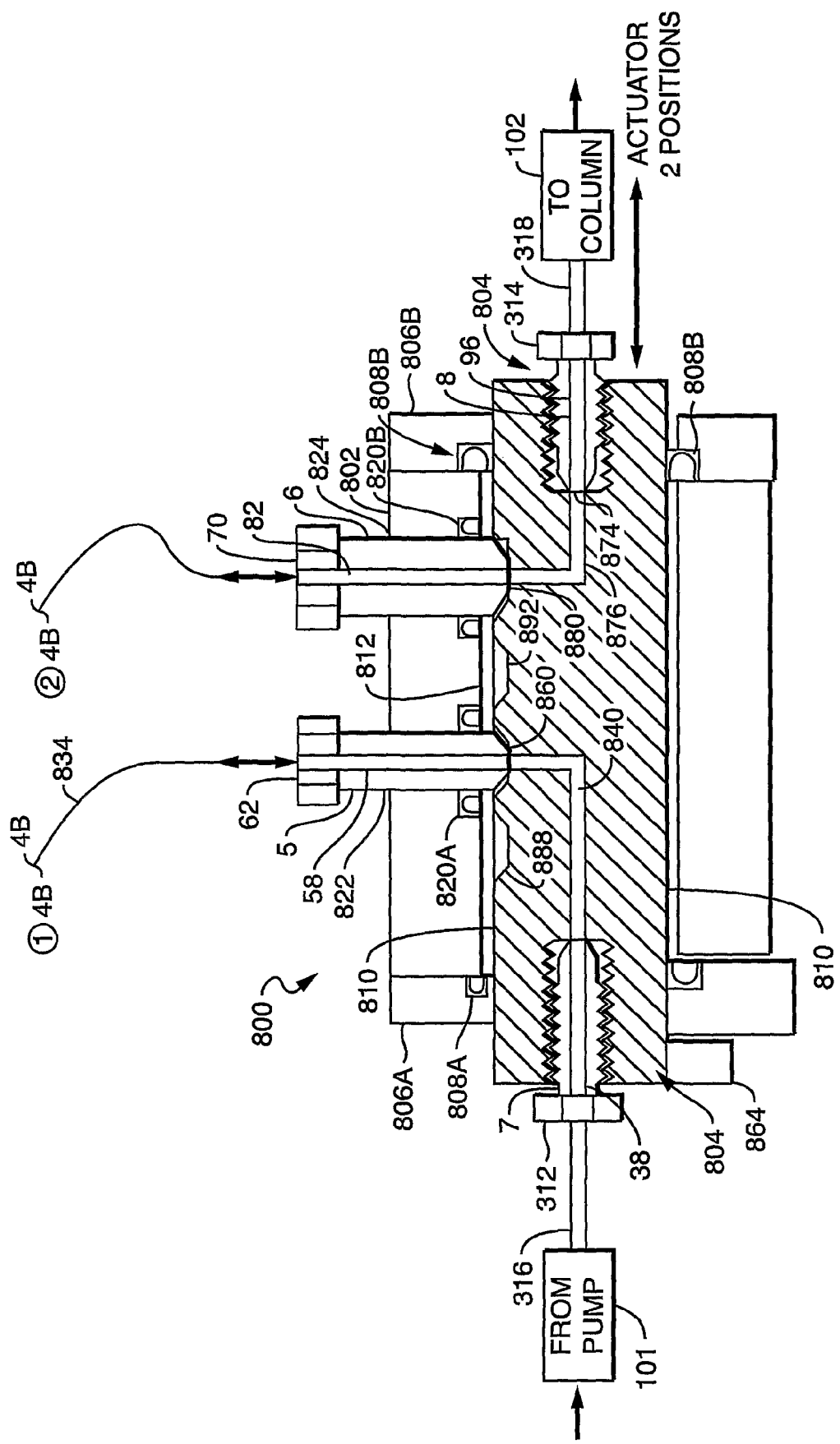
FIG. 4A is a separated elevation section view at break lines 4B of another embodiment of the present invention as a multiple valve comprised of a linear isolation valve and a linear injection valve.
Figure 4B:
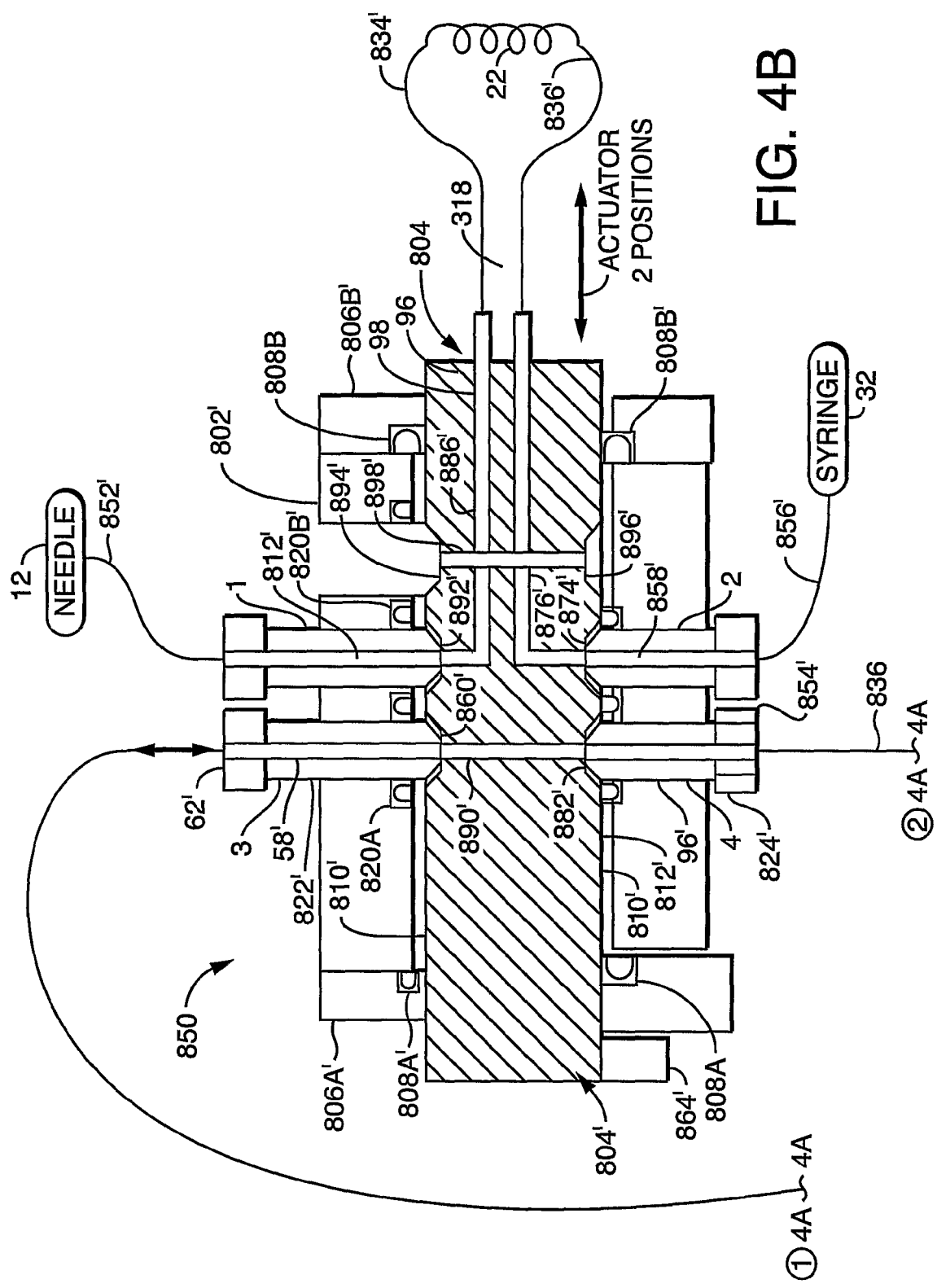
FIG. 4B is a separated elevation view at break lines 4A of the embodiment of FIG. 4B.

In a second embodiment, FIGS. 4A and 4B illustrate a combination linear flow through isolation valve 800 and linear flow through injection valve 850 each of which has a configuration similar to the generally cylindrically shaped second embodiment of rotor 61 illustrated in FIGS. 2A and 2B. The linear flow through isolation valve 800 is comprised of a stationary member 802 and a movable member 804. The movable member 804 is similar to the rotor 202 except that instead of moving in a rotary motion, the movable member 804 moves by sliding linearly through the stationary member 802. The movable member 804 can have any other type of cross-section such as, for example but not limited to, an oval shape or a square with smooth rounded corners. The rotary member 804 is made preferably of either a metal or a polymer or sapphire.

The stationary member 802 is comprised of two surfaces 806a and 806b which surround the movable slider member 804. The two surfaces 806a and 806b each include self-energized lip seals 808a and 808b. The stationary member 802 also forms an interfacing surface 810 surrounding the movable member Tube fitting 7 from the high pressure pump 101 is inserted into port 352 of the movable member 804 where it is sealed in a manner as to substantially prevent external leakage. Flow is provided from the high pressure pump 101 to the pin fitting 7 by means of flexible conduit 316 and coupling 312. The internal conduit 38 within the fitting 7 is in fluidic communication with internal conduit 840 within the movable member 804 and with an open port 860 on the interfacing surface 810. The open port 860 is in fluidic communication with a chamber or volume of space 812 within the stationary member 802 that is bordered by the interfacing surface 810. The volume of space 812 within the stationary member 802 and the movable member 804 are sealed by the self-energized lip seals 808a and 808b. Isolation pin valve 5 penetrates through stationary member 802 at penetration 822 such that the pin valve 5 can move linearly up and down.

By means of coupling 62, the internal conduit 58 within pin valve 5 is in fluidic communication with conduit tubing 834 to the isolation pin valve 3 of linear flow through injection valve 850. Conduit tubing 66 from the face seal valve 10 is then fluidically coupled to the internal conduit 82 of isolation pin valve 78 by means of coupling 70.

Similarly, isolation valve pin 6 penetrates through stationary member 802 at penetration 824 such that the pin valve 6 can move linearly up and down. The internal conduit 82 within isolation pin valve 78 is then in fluidic communication with the volume of space 812 within the stationary member 802 that is bordered by the interfacing surface 810. The pin valve 6 is positioned to interface with open port 880 on the interfacing surface 810. The open port 880 is in fluidic communication with the volume of space 812.

To seal the pin isolation valves 5 and 6, the stationary member 802 includes self-energized lip seals 820a and 820b, respectively. The lip seals are commercially available from Furon, Inc. of Hoosick Falls, N.Y.

During the injection phase, the internal conduit 82 within the pin isolation valve 6 is in fluidic communication also with internal conduit 876 within the movable member 804 and with an open port 874 on an opposite end of movable member 804. Fitting 8 is inserted into open port 874 so that the internal conduit 96 within fitting 8 is in fluid communication with a sample loop 22. The internal conduit 96 within the fitting 8 is in fluidic communication with the column by means of flexible conduit 318 that is coupled to the fitting 8 by coupling 314.

During the load phase, the pin isolation valve 6 is positioned to interface with blank port 892 on the surface 810 of movable member 804. Similarly, the pin isolation valve 5 is positioned to interface with blank port 888 on the surface 810 of movable member 804. These actions effectively isolate flow from the high pressure pump to the linear flow through injection valve 850 and to the column in the same manner as discussed previously for the first embodiment.

A means for moving the moving member 804 laterally is provided such as, but not limited to, a linear motor 864 which is coupled to the moving member 804 enables the pins 5 and 6 to be shifted between the open ports 860 and 880 and the blank ports 888 and 892, respectively.

The linear flow through injection valve 850 is analogous to the rotary injection valve 300. The linear valve 850 comprises stationary member 802' and a movable member 804'. The two members 802' and 804' interface at surface 810'. The movable member 804' slides along the surface 810' while the stationary member 802' remains in place. In this configuration, isolation pin valve 3, having an internal conduit 58' and which receives the fluid flow transferred from the high pressure pump through flexible conduit 834, penetrates the stationary member 802' at port 822'. The isolation pin valve 3 is coupled to conduit 834 by means of coupling 62' and is movably disposed within the stationary member 802' such that isolation pin valve 3 can move up and down and so that the internal conduit 58 of pin valve 3 is in fluidic communication with a first opening 860' of a flow through internal conduit 890' that passes through the movable member 804' to second opening 880'. Both the first opening 860' and the second opening 882' interface with a chamber or volume of space 812' within the stationary member 802' that is bordered by the interfacing surface 810'. The stationary member 802' and the movable member 804, act to seal the chamber 812'.

Isolation pin valve 4 is movably disposed within the stationary member 802' in second opening 880' such that isolation pin valve 4 is in fluidic communication with the second opening 880' of the enclosed flow through channel 890'. Isolation pin valve 4, having an internal conduit 96 and which transfers the fluid flow from the high pressure pump 101 to the column 102 through flexible conduit 836, penetrates the stationary member 802' at port 824' and is coupled to flexible conduit 836 by means of coupling 854'. The flexible conduit 836 is coupled to the isolation pin valve 6 of linear isolation valve 800 by means of coupling 70.

Flexible conduit 852' is fluidically coupled to needle 12 to fluidically couple with the internal conduit 812' of isolation pin valve 1 which is movably disposed within the stationary member 802' such that isolation pin valve 1 can move up and down and so that the internal conduit 812' of pin valve 1 is in fluidic communication with a first opening 892' of an enclosed flow through channel 886' that passes through the movable member 804' to fluidically couple to the sample loop 22 through flexible conduit 834'.

Syringe 32 is fluidically coupled to flexible conduit 856' which in turn fluidically couples with the internal conduit 858' of isolation pin valve 2 which is movably disposed within the stationary member 802' such that isolation pin valve 2 can move up and down and so that the internal conduit 858' of pin valve 2 is in fluidic communication with a first opening 874' of a flow through internal conduit 876' that passes through the movable member 804' to fluidically couple to the sample loop 22 through flexible conduit 836'.

Open ports 894' and 896' in movable member 804' serve as ends of flow through internal conduit 898' so that when pin 1 and pin 2 are re-positioned to interface with open ports 894' and 896', respectively, the needle 12 and syringe 32 are then fluidically coupled directly to each other and disconnected from the sample loop 22.

The stationary member 802' is comprised of two surfaces 806a' and 806b' which surround the movable slider member 804'. The two surfaces 806a' and 806b' each include self-energized lip seals 808a' and 808b'. The stationary member 802' also forms an interfacing surface 810' surrounding the movable member 804'.

To seal the isolation pin valves 1, 2, 3 and 4, the stationary member 802' includes self-energized lip seals 820a' and 820b', respectively.

A means for moving the moving member 804' laterally is provided such as, but not limited to, a linear motor 864' which is coupled to the moving chamber 804' enables the pins 1 and 2 to be shifted between the open ports 892' and 874', and the open ports 894' and 896', respectively. The linear motor 864' can be driven by any means known in the art such as by electrical, hydraulic or pneumatic power.

During the load phase, the isolation pin valve 3 is positioned to interface with opening 860' on the surface 810' of movable member 804'. Similarly, the isolation pin valve 4 is positioned to interface with opening 880' also on the surface 810' of movable member 804'. These actions effectively isolate flow from the high pressure pump 101 to the sample loop 22 since the flow from the pump 101 is now recirculated from pin valve 3 through internal conduit 890' to the column 102 through isolation pin valve 4.

The needle 12 is then fluidically coupled to the sample loop 22 by means of the internal conduit 812' of isolation pin valve 1 being fluidically coupled to the opening 894' of internal conduit 898'. Correspondingly, the syringe 32 is fluidically coupled to the sample loop 22 by means of the internal conduit 898' being fluidically coupled to opening 896' of internal conduit 876'. The syringe 32 is then used to aspirate the sample fluid into the sample loop 22 from the needle 12.

During the transition phase, the moving member 804' is shifted laterally so that isolation pin valve 1 interfaces with opening 894' and isolation pin valve 2 interfaces with opening 896', thereby isolating flow from the needle 12 to the syringe 32. Correspondingly, the internal conduit 58' of isolation pin valve 3 interfaces with opening 892' of internal conduit 886'. Internal conduit 96' of isolation pin valve 4 interfaces with opening 874' of internal conduit 876'.

During the injection phase, as a result of the shifting of the moving member 804' during the transition phase, flow from the pump 101 through isolation valve 800 is then channeled through the sample loop 22 and on to the column 102 through the isolation valve 800.

Another variation of the second embodiment is to design the stationary member 802 and the moving member 804 as a duplex or mirror-image design so that the moving member 804 further comprises ports and internal conduits for the pump and column, or a second pump and column, to be capable of serving a second face seal valve simultaneously.

Although described with respect to application to high pressure fluids, the various embodiments of the present invention can be applied to fluids at any operating pressure, including sub-atmospheric, i.e., vacuum applications as well.

The invention has been described herein with reference to particular exemplary embodiments. Certain alterations and modifications may be apparent to those skilled in the art, without departing from the scope of the invention. The exemplary embodiments are meant to be illustrative, not limiting of the scope of the invention, which is defined by the appended claims.

What is claimed is:

1. A flow through injection valve, said flow through injection valve comprising:
   a stationary member;
   a movable member, a surface of said stationary member interfacing with a surface of said movable member, said movable member including an opening; and
   at least one pin valve having a pin and a flow through internal conduit extending through said pin;
   said pin extending through said opening to directly abut at least one flow through conduit at a bottom region of said opening of said movable member;
   said at least one pin valve movably disposed so that said flow through internal conduit extending through said pin is capable of fluidically communicating with said at least one flow through conduit in said movable member,
   said at least one pin valve movably disposed so that said flow through internal conduit of said pin is capable of fluidically communicating with another flow through conduit in said movable member.

2. The flow through injection valve according to claim 1, wherein one of said at least one pin valve is fluidically coupled to a sample loop of a high pressure liquid chromatography (HPLC) system.

3. The flow through injection valve according to claim 1, wherein one of said at least one pin valve is in fluidic communication with a pump supplying high pressure liquid to a high pressure liquid chromatography (HPLC) system.

4. The flow through injection valve according to claim 1, wherein one of said at least one pin valve is fluidically coupled to a column discharging high pressure liquid from a high pressure liquid chromatography (HPLC) system.

* * * * *